(12) United States Patent
Eckman

(10) Patent No.: US 6,726,690 B2
(45) Date of Patent: Apr. 27, 2004

(54) DISKECTOMY INSTRUMENT AND METHOD

(75) Inventor: Walter W. Eckman, Tupelo, MS (US)

(73) Assignee: Concept Matrix, LLC, Orlando, FL (US)

( * ) Notice: Subject to any disclaimer, the term of this patent is extended or adjusted under 35 U.S.C. 154(b) by 0 days.

(21) Appl. No.: 10/345,525

(22) Filed: Jan. 16, 2003

(65) Prior Publication Data

US 2003/0135218 A1 Jul. 17, 2003

Related U.S. Application Data

(60) Provisional application No. 60/369,701, filed on Apr. 2, 2002, and provisional application No. 60/349,742, filed on Jan. 17, 2002.

(51) Int. Cl.⁷ .............................................. A61B 17/32
(52) U.S. Cl. ........................................ 606/79; 606/170
(58) Field of Search ...................... 606/79, 80, 81, 606/170, 167, 180

(56) References Cited

U.S. PATENT DOCUMENTS

| | | | | |
|---|---|---|---|---|
| 3,967,377 A | * | 7/1976 | Wells ........................... | 30/320 |
| 4,473,076 A | * | 9/1984 | Williams et al. ............ | 128/305 |
| 4,499,898 A | * | 2/1985 | Knepshield et al. ........ | 128/305 |
| 4,884,569 A | * | 12/1989 | Fedorov et al. ............. | 128/305 |
| 5,203,865 A | * | 4/1993 | Siepser ........................ | 606/166 |
| 5,209,799 A | * | 5/1993 | Vigil ............................ | 156/156 |
| 5,403,276 A | | 4/1995 | Schechter et al. | |
| 5,445,639 A | | 8/1995 | Kuslich et al. | |
| 5,620,453 A | * | 4/1997 | Nallakrishnan ............. | 606/166 |
| 5,645,549 A | | 7/1997 | Boyd et al. | |
| 5,669,876 A | | 9/1997 | Schechter et al. | |
| 5,685,840 A | | 11/1997 | Schechter et al. | |
| 5,797,939 A | * | 8/1998 | Yoon ........................... | 606/167 |
| 5,827,305 A | * | 10/1998 | Gordon ........................ | 606/159 |
| 5,833,692 A | * | 11/1998 | Cesarini et al. ............. | 606/79 |
| 5,885,292 A | | 3/1999 | Moskovitz et al. | |
| 5,908,432 A | * | 6/1999 | Pan ............................ | 606/167 |
| 5,928,239 A | | 7/1999 | Mirza | |
| 5,935,144 A | * | 8/1999 | Estabrook ................... | 606/169 |
| 6,171,312 B1 | * | 1/2001 | Beaty .......................... | 606/80 |
| 6,383,188 B2 | | 5/2002 | Kuslich et al. | |
| 2002/0138078 A1 | | 9/2002 | Chappuis | |

* cited by examiner

Primary Examiner—Eduardo C. Robert
Assistant Examiner—David Comstock
(74) Attorney, Agent, or Firm—Akin Gump Strauss Hauer & Feld, L.L.P.

(57) ABSTRACT

A diskectomy instrument includes an elongate body, a blade and a drive stem. The elongate body has a distal end, a proximal end, and a blade opening proximate the distal end. The blade is removably and movably mounted within the elongate body proximate the blade opening. The blade has a distal end, a proximal end, a sharp edge, a ramped portion and a stem mating portion. The drive stem is movably mounted within the elongate body and has a distal end, a proximal end and a blade mating portion. The drive stem is configured to slidably engage the blade when the drive stem is moved distally thereby extending the at least one blade radially outward though the at least one blade opening. The blade mating portion is configured to cooperatively engage the stem mating portion of the blade when the drive stem is moved proximally thereby retracting the blade.

31 Claims, 8 Drawing Sheets

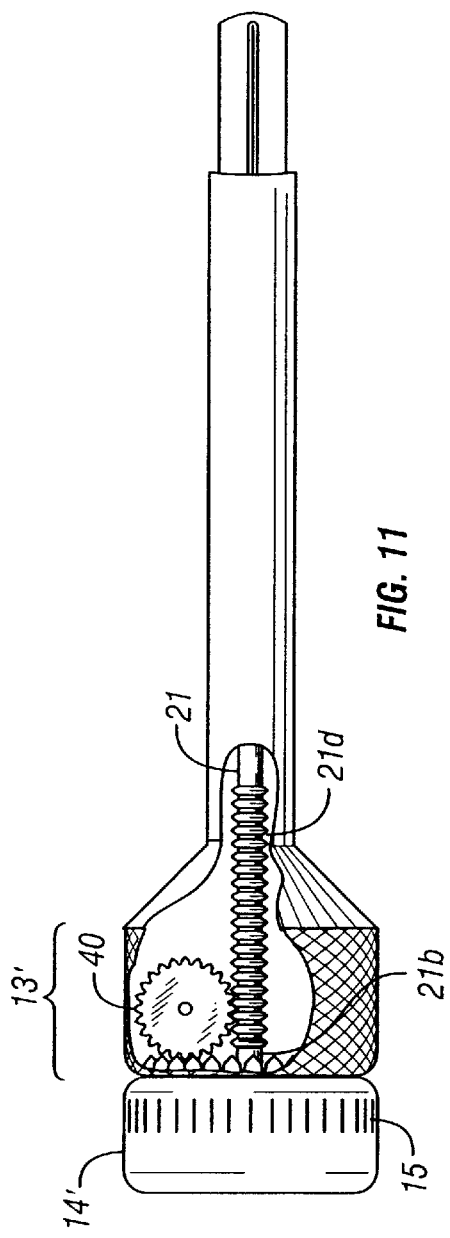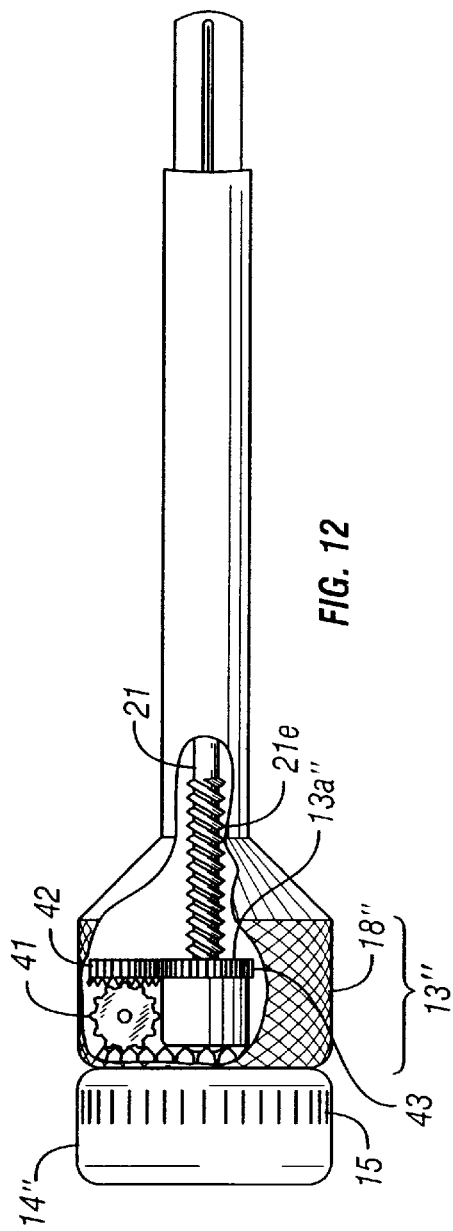

DISKECTOMY INSTRUMENT AND METHOD

CROSS-REFERENCES TO RELATED APPLICATIONS

This application claims the benefit of U.S. Provisional Application No. 60/369,701 filed Apr. 2, 2002 entitled "DISKECTOMY INSTRUMENT AND METHOD" and U.S. Provisional Application No. 60/349,742 filed Jan. 17, 2002 entitled "DISKECTOMY INSTRUMENT AND METHOD," the entire contents of which are incorporated by reference herein.

BACKGROUND OF THE INVENTION

The present invention relates to an apparatus and method for performing diskectomy and more particularly to an instrument for performing partial diskectomies utilizing minimally invasive surgical techniques and a method for using the instrument.

Referring to prior art FIGS. 9 and 10, the spine 120, also known as the vertebral column or the spinal column, is a flexible column of vertebrae 100 (special types of bones) held together by muscles, ligaments and tendons. The spine 120 extends from the cranium (not shown) to the coccyx 126, encasing a spinal cord 128 and forming the supporting axis of the body (not shown). The spinal cord 128 is a thick bundle of nerve tissue (nerves) that branch off to various areas of the body for the purposes of motor control, sensation, and the like. The spine 120 includes seven cervical vertebrae (not shown), twelve thoracic vertebrae (not shown), five lumbar vertebrae, $L^I$–$L^V$, five sacral vertebrae, $S^I$–$S^V$, and three coccyx vertebrae 126. The sacral and coccyx vertebrae are each fused, thereby functioning as a single unit. FIG. 10 shows the lumbar region 122, the sacral region 124 and the coccyx 126 of the spine 120 and that the vertebrae 100 are stacked one upon another. The top portion 100a and bottom portion 100b of each vertebrae 100 is slightly concave. The opposing concave vertebral surfaces form the intervertebral space 121 in which an intervertebral disk (not shown) resides. Each of the intervertebral disks has a soft core referred to as a nucleus pulposus or nucleus (not shown).

In FIG. 9, directional arrow 101a is pointing in the posterior direction and directional arrow 101b is pointing in the anterior direction. FIG. 9 shows that each vertebrae 100 includes a body 106 in the innermost portion, a spinal canal 108 and a spinous process 102 at the posterior-most end of the vertebra 100. The vertebrae 100 are substantially similar in composition, but vary in size from the larger lumbar to the smallest coccyx vertebrae 126. Each vertebrae 100 further includes two transverse processes 104 located on either side and a protective plate-like structure referred to as a lamina 110. Nerves from the spinal cord 128 pass through the spinal canal 108 and foramina 111 to reach their respective destinations within the body.

The natural aging process can cause a deterioration of the intervertebral disks, and therefore, their intrinsic support strength and stability is diminished. Sudden movements may cause a disk to rupture or herniate. A herniation of the disk is primarily a problem when the nucleus pulposus protrudes or ruptures into the spinal canal 108 placing pressure on nerves which in turn causes spasms, tingling, numbness, and/or pain in one or more parts of the body, depending on the nerves involved. Further deterioration of the disk can cause the damaged disk to lose height and as bone spurs develop on the vertebrae 100, result in a narrowing of the spinal canal 108 and foramen 111, and thereby causes pressure on the nerves emanating from the spinal cord 128.

Presently, there are several techniques, in addition to non-surgical treatments, for relieving the symptoms related to intervertebral disk deterioration. Surgical options include chemonucleolysis, laminectomy, diskectomy, microdiskectomy, and spinal fusion.

Chemonucleolysis is the injection of an enzyme, such as chymopapain, into the disk to dissolve the protruding nucleus pulposus. The enzyme is a protein-digesting enzyme and is used to dissolve the disk material. Since the enzyme is essentially a tissue-dissolving agent, it is indiscriminate in the protein-based matter it dissolves. Should the enzyme be injected into the wrong place, or if there is a breach in the disk capsule that would allow the solution to enter the spinal canal or to contact nerve tissue or the like, the resultant damage to nerve tissue could not be reversed. Even worse, about half of the patients who receive chemonucleolysis treatments experience increased back pain and muscle spasms immediately after the injection and more than half have incapacitating back pain for durations up to three months after such treatments.

A laminectomy is performed to decompress the spinal canal 108 by open surgical techniques under general anesthesia. In this procedure, the lamina 110, (the bone that curves around and covers the spinal canal 108 as shown in FIG. 9), and any disk tissue causing pressure on a nerve or the spinal canal 108, are partially removed. This technique is highly invasive and traumatic to the body, and therefore requires an extended recovery time of about five weeks and a hospital stay of a few days. In addition to the trauma inflicted on the body from even a successful surgery, there are increased risks of future problems due to the removed portion of the lamina 110 which is no longer in place to support and protect the spinal canal 108 at the area where the surgery took place. Further, the vertebrae 100 may shift due to the lack of support in the structure. Thus, simply removing the disk and parts of the vertebral bone is a short-term, pain-relieving corrective action but not a long-term solution.

Diskectomy is a form of spinal surgery wherein part or all of an intervertebral disk is excised typically through open surgical techniques. Recently, less invasive techniques referred to as percutaneous diskectomy or microdiskectomy have been developed to reduce the surgical trauma to the patient. In microdiskectomy, a much smaller incision is made than in normal open surgeries. A small retractor, working channel or tube is inserted through the posterior muscles (not shown) to allow access to the damaged or herniated disk. Surgeons utilize special surgical instruments modified to work in such small openings such as curettes, osteotomes, reamers, probes, retractors, forceps, and the like to cut and remove part of the disk while monitoring their technique using a microscope, fluoroscope (real-time X-ray monitoring), and/or an endoscope (a miniature TV camera with associated viewing monitor). While this technique is much less invasive than conventional open surgeries, due to their design the instruments presently available tend to extend the length of time of the surgery and may cause possible damage to areas other than the herniated disk. For example, the curette is a spoon-shaped instrument with a sharp edge that is used mainly to scrape the nucleus pulposus matter (not shown) from the end plates of the vertebral bones. Since the blade is unprotected, there is potential for damage to the surrounding nerves and ligaments during insertion and during use. Further, due to the varying concavity of the vertebral space (or the concavity of the top and bottom portions 100a,b of the vertebral bones) it is often a time consuming procedure for the surgeon to repeatedly scrape at varying angles using the curette. Another instrument that is often used is the reamer (not shown) which is intended to remove the nucleus pulposus matter more quickly than a curette. The reamer is usually a cylindrically-shaped, drill-bit-like device with a flat tip and a plurality of sharp edges along its outer sides. The reamer is continuously turned inside the vertebral disk space 121 to scrape the nucleus pulposus matter from the vertebral bones; however, reamers often cause damage to adjacent vertebrae and may cause damage to nerves, blood vessels and/or ligaments while being inserted into the intervertebral space.

The removal of a significant amount of disk material or numerous surgeries often increases the instability of the spine 120 thereby necessitating spinal fusion surgery. In a fusion procedure, a damaged disk may be completely removed. Parts of a bone from another part of the body, such as the pelvis, are harvested, and the bone parts or grafts are subsequently placed between the adjacent vertebrae 100 so that the adjacent vertebrae 100 grow together in a solid mass. In the fusion surgery, which is presently performed as an open surgical technique, the posterior lamina 110 and the centers of the vertebral bodies 106 may both be cut. The surgery often involves consequential damage to the associated posterior ligaments, muscles and joints in addition to the removal of part or all of the lamina 110. The recovery time for a normal spinal fusion surgery is significant due not only to the fact that normal movement cannot be allowed until detectable bone growth has occurred between the bone grafts and the adjacent vertebrae 100, but the associated ligaments, muscles and the location where the bone grafts were harvested must also recover. Oftentimes portions of the spine 120 must be immobilized during the recovery period causing added discomfort and inconvenience to the patient.

What is required, but not presently provided by the prior art devices and methods, is a surgical instrument for performing partial diskectomies that is minimally invasive, easy to use, safe to insert into the body during surgery, provides rapid removal of the nucleus pulposus matter, and which does not cause undesired damage to adjacent vertebrae. What is further required is a micro surgical technique that allows for fast patient recovery times and that can be used on an outpatient basis.

BRIEF SUMMARY OF THE INVENTION

Briefly stated, the present invention comprises a diskectomy instrument. The diskectomy instrument includes an elongate body, at least one blade and a drive stem. The elongate body has a distal end and a proximal end. The elongate body has at least one blade opening proximate the distal end. The at least one blade is removably and movably mounted at least partially within the elongate body proximate the at least one blade opening. The at least one blade has a distal end, a proximal end, at least one sharp edge extending at least partially between the distal end and the proximal end, a ramped portion and a stem mating portion. The drive stem is movably mounted within the elongate body. The drive stem has a distal end, a proximal end and a blade mating portion. The drive stem is configured to slidably engage the at least one blade when the drive stem is moved distally thereby extending the at least one blade radially outward though the at least one blade opening. The blade mating portion is configured to cooperatively engage the stem mating portion of the blade when the drive stem is moved proximally thereby retracting the at least one blade.

The present invention further comprises a diskectomy instrument including an elongate body, a plurality of blades and a drive stem. The elongate body has a distal end and a proximal end. The elongate body has a plurality of blade openings proximate the distal end. The plurality of blades are removably and movably mounted at least partially within the elongate body. Each blade is disposed proximate to a respective one of the plurality of blade openings. The plurality of blades each have a distal end, a proximal end, at least one sharp edge extending at least partially between the distal end and the proximal end, a ramped portion and a stem mating portion. The drive stem is movably mounted within the elongate body and has a distal end, a proximal end and a blade mating portion. The drive stem is configured to slidably engage each of the plurality of blades when the drive stem is moved distally thereby extending the plurality of blades radially outward though the respective plurality of blade openings. The blade mating portion is configured to cooperatively engage the stem mating portion of each of the plurality of blades when the drive stem is moved proximally thereby retracting the plurality of blades.

The present invention further comprises a diskectomy blade having a distal end and a proximal end for use in a diskectomy instrument. The diskectomy instrument includes a drive stem having a blade mating portion. The blade includes at least one sharp edge, a ramped portion and a stem mating portion. The at least one sharp edge extends at least partially between the distal end and the proximal end. The ramped portion is configured to slidably engage one of the drive stem and the body of the diskectomy instrument. The stem mating portion is configured to couple with the blade mating portion of the diskectomy instrument.

The present invention further comprises a method of using a diskectomy instrument. The diskectomy instrument includes an elongate body having a blade opening, a blade having a sharp edge, a ramped portion and a stem mating portion. The diskectomy instrument also includes a drive stem having a blade mating portion. The drive stem is configured to slidably engage the at least one blade when the drive stem is moved distally thereby extending the blade radially outward though the blade opening. The blade mating portion of the drive stem is configured to cooperatively engage the stem mating portion of the blade when the drive stem is moved proximally thereby retracting the blade. The method includes the step of moving the drive stem proximally causing the blade mating portion to engage the stem mating portion of the blade thereby retracting the blade at least partially into the elongate body. The method also includes the steps of inserting a distal end of the diskectomy instrument into a small gap between a first vertebra and a second vertebra of a spine and moving the drive stem distally causing the blade mating portion to engage the blade which in turn moves the blade distally and radially outward. The method further includes the steps of rotating the blade in a cutting direction defined by the orientation of the sharp edge and moving the drive stem proximally causing the blade mating portion to engage the stem mating portion of the blade thereby retracting the blade at least partially into the elongate body. The method further includes the step of withdrawing the distal end of the diskectomy instrument from the small gap.

The present invention further comprises a method of using a diskectomy instrument and a working tube in outpatient surgery. The diskectomy instrument includes an elongate body having a blade opening, a blade having a sharp edge and a partially convex shape, a ramped portion and a stem mating portion. The diskectomy instrument also includes a drive stem having a blade mating portion. The drive stem is configured to slidably engage the at least one blade when the drive stem is moved distally thereby extending the blade radially outward though the blade opening. The blade mating portion is configured to cooperatively engage the stem mating portion of the blade when the drive stem is moved proximally thereby retracting the blade. The method includes the step of moving the drive stem proximally causing the blade mating portion to engage the stem mating portion of the blade thereby retracting the blade at least partially into the elongate body. The method also includes the steps of inserting a distal end of the working tube proximate a small gap between a first vertebra and a second vertebra of a spine accessible through an incision between about 10 mm and about 100 mm in span and inserting a distal end of the diskectomy instrument into the working tube in order to access the intervertebral space between the first and second vertebrae. The method includes the steps of moving the drive stem distally causing the drive stem to engage the blade which in turn moves the blade distally and radially outward and rotating the blade in a cutting direction defined by the orientation of the sharp edge so that the convexly-shaped blade finds the most concave portions of the first and second vertebrae. The method includes the steps of moving the drive stem proximally causing the blade mating portion to engage the stem mating portion of the blade thereby retracting the blade at least partially into the elongate body and withdrawing the distal end of the diskectomy instiument from the working tube.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 11 is a side elevational view of a first actuator mechanism for a diskectomy instrument in accordance with the present invention;

FIG. 12 is a side elevational view of a second actuator mechanism for a diskectomy instrument in accordance with the present invention.

DETAILED DESCRIPTION OF THE INVENTION

Figure 1:
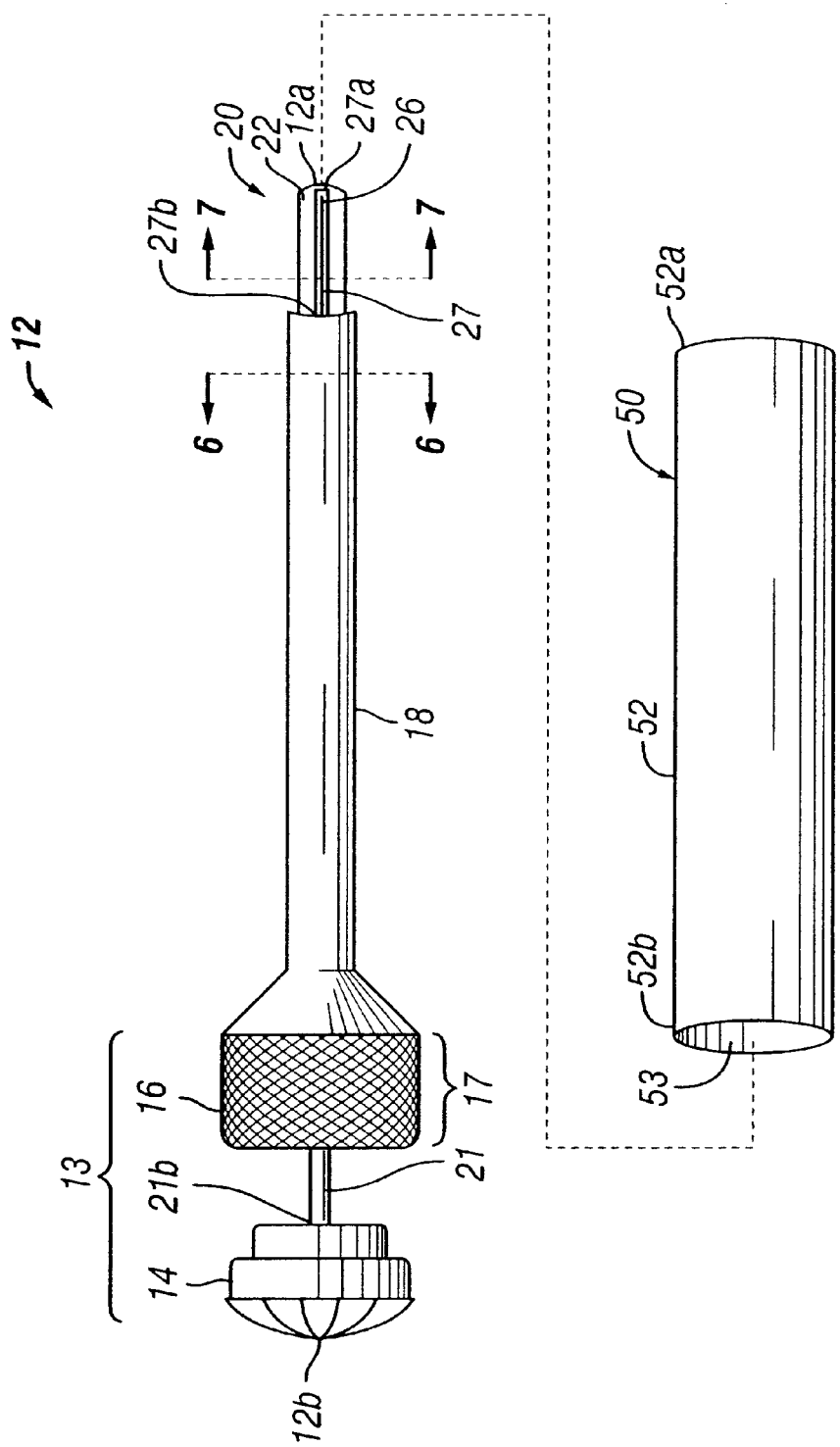
FIG. 1 is a side elevational view of a diskectomy instrument in accordance with the preferred embodiment of the present invention.

Certain terminology is used in the following description for convenience only and is not limiting. The words "right", "left", "lower", and "upper" designate directions in the drawing to which reference is made. The words "inwardly" and "outwardly" refer direction toward and away from, respectively, the geometric center of the diskectomy instrument and designated parts thereof. The terminology includes the words above specifically mentioned, derivatives thereof and words of similar import. Additionally, the word "a", as used in the claims and in the corresponding portions of the specification, means "at least one."

Referring to the drawings in detail, wherein like reference numerals indicate like elements throughout, there is shown in FIG. 1 a diskectomy instrument 12 in accordance with a preferred embodiment of the present invention. The diskectomy instrument 12 includes an elongate body 18, a probe assembly 20, an actuator mechanism 13, a blade positioning knob 14 and a handle or blade rotation knob 16. The diskectomy instrument 12 has a distal end 12a and a proximal end 12b. Obviously, the probe assembly 20 can be integral or part of the elongate body 18. The portions of the diskectomy instrument 12 intended to contact internal human body matter are formed of a biologically compatible material selected such as stainless steel, titanium, nickel plated metal, any biocompatible metal or alloy, a biocompatible ceramic, a biocompatible polymeric material and the like.

The elongate body 18 is between about 5 mm and 30 mm in diameter making it ideally suited for use in outpatient minimally invasive surgery. Preferably, the diskectomy instrument 12 is used in combination with a working tube 50 of only slightly greater diameter which provides a portal to the small gap between two adjacent vertebrae 100 as will be described in greater detail hereinafter. The working tube 50 preferably has an elongate housing 52 having a distal end 52a, a proximal end 52b and an interior lumen 53 traversing through the elongate housing 52. The working tube is configured to be inserted through an incision between about 5 mm and about 100 mm in span, but is more preferably configured to be inserted through an incision of less than about 25 mm in span. Of course the working tube 50 and the diskectomy tool 12 can be configured to be inserted through incisions or openings having other dimensions and can be used in conventional open surgery without departing from the present invention.

Figure 2:
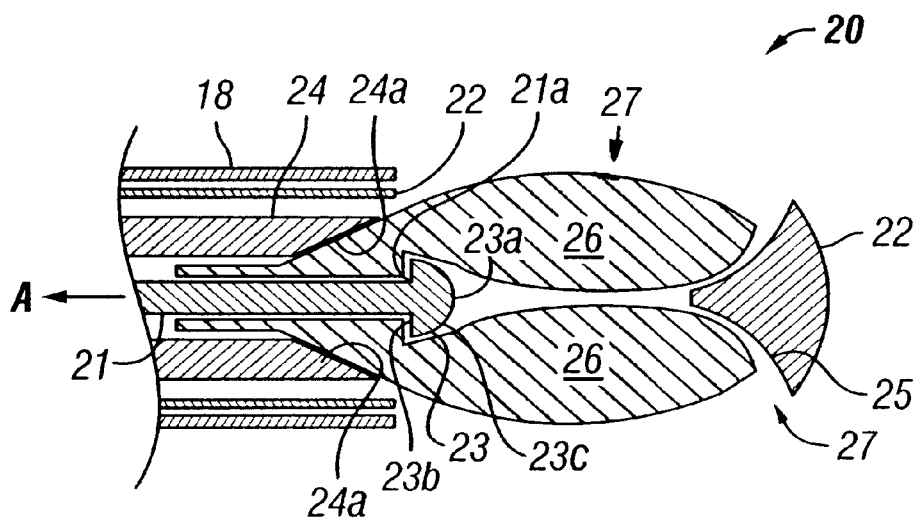
FIG. 2 is a greatly enlarged side sectional view of a portion of the diskectomy instrument of FIG. 1 in a retracted position.

FIG. 2 shows a side cutaway of the distal end 12a of the diskectomy instrument 12 providing a much more detailed view of the probe assembly 20. The probe assembly 20 includes a probe body 22, a drive stem 21, an inner sheath 24, a biasing cone 25 and at least one blade 26. The probe body 22 includes a blade opening 27 for each blade 26. The blade opening 27 has a distal end 27a and a proximal end 27b. Preferably each blade opening 27 is generally rectangularly-shaped. But, the blade openings 27 may be other shapes. The blade openings 27 are selected to be only slightly wider than the blades 26 in order to provide lateral support to the blades 26 when the blades 26 are radially extended. The close tolerance between the blade openings 27 and the blades 26 also assists in preventing foreign materials from being trapped in between the blades 26 and the blade openings 27 when the blades 26 are being retracted.

The drive stem 21 has a distal end 21a and a proximal end 21b (FIG. 1). A stem end-cap 23 is positioned on the distal end 21a of the drive stem 21 and includes a proximal end 23b and a distal end 23a, the distal end preferably being configured as a dome-shaped or rounded conically-shaped surface 23c as discussed more fully below. The proximal end 23b and the dome-shaped surface 23c of the stem end-cap 23 form a blade mating portion 23b, 23c of the drive stem 21. The drive stem 21 is slidably mounted within the probe 20 and is configured to slidably engage the blades 26 when the drive stem 21 is moved distally thereby moving the blades 26 distally and extending the blades 26 radially outward through the blade openings 27. The drive stem 21, or more particularly, the blade mating portion(s) 23b, 23c of the drive stem 21 is configured to cooperatively engage a stem mating portion 29 of the blades 26 when the drive stem 21 is moved proximally thereby moving the blades 26 proximally and retracting the blades 26 radially inward. Of course other more complicated mechanical arrangements may be coupled between the drive stem 21 and the blades 26 without departing from the present invention.

Figure 7:
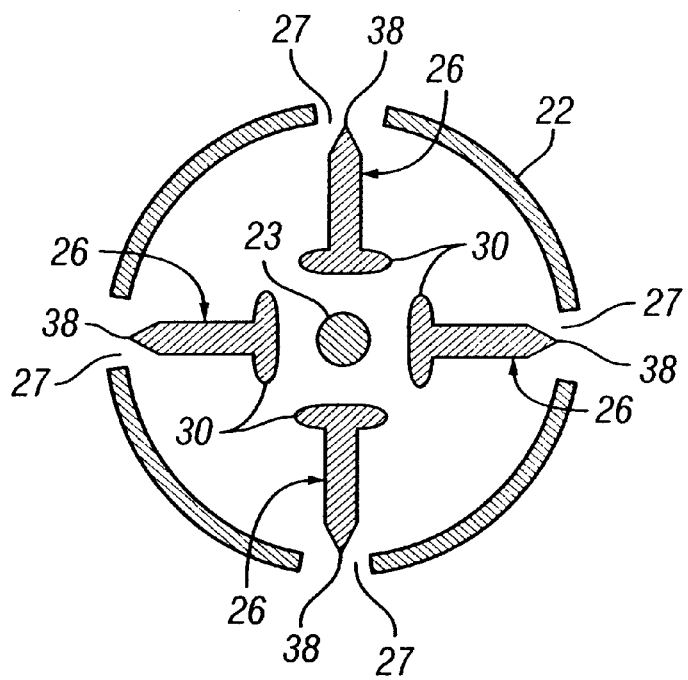
FIG. 7 is a greatly enlarged sectional view of a portion of the diskectomy instrument taken along line 7—7, FIG. 1.
Figure 8:
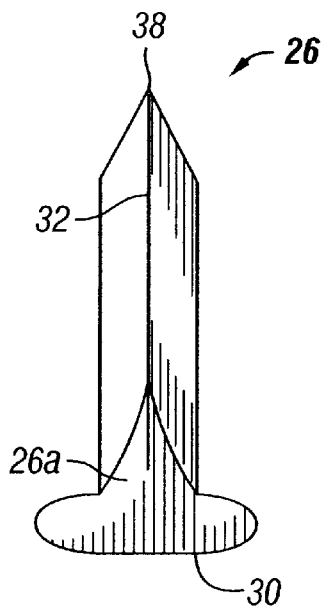
FIG. 8 is a front elevational view of the blade of FIG. 4.

Preferably, there are four blades 26 (see FIGS. 7 and 8). When configured with four or more blades 26, the diskectomy tool 12 is more stable during a cutting procedure and can more easily find the most concave portions 100a or 100b of a particular vertebra 100. But, there may be any number of blades 26 without departing from the spirit of the invention. Each of the blades 26 (FIGS. 4–5) is preferably identical and includes a distal end 26a and proximal end 26b. It is contemplated, however, that the blades 26 need not be identical to one another and that the blades 26 may also be matched in opposing pairs or may each be unique with respect to the others.

Figure 4:
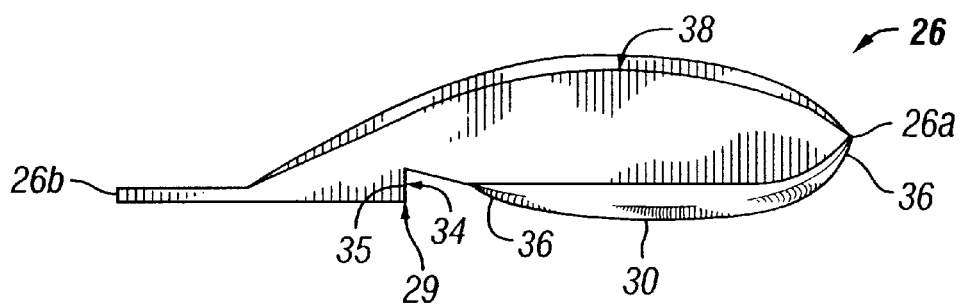
FIG. 4 is a side elevational view of a blade used in a diskectomy instrument in accordance with the present invention.
Figure 5:
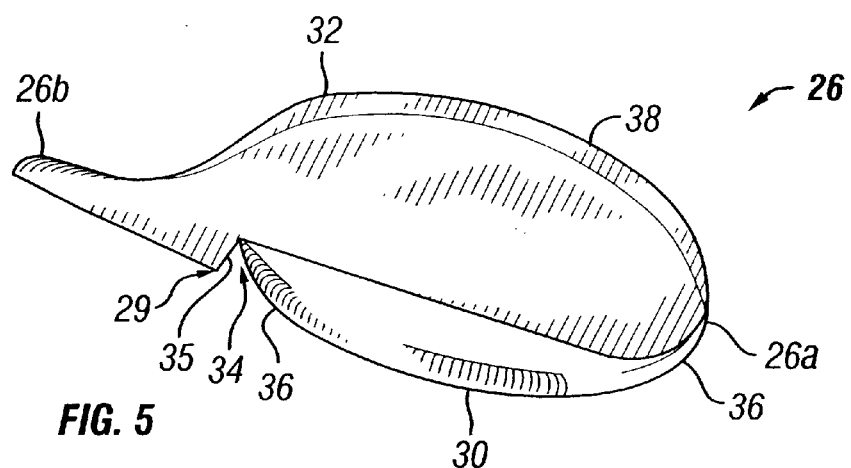
FIG. 5 is a perspective view of the blade of FIG. 4.
Figure 6:
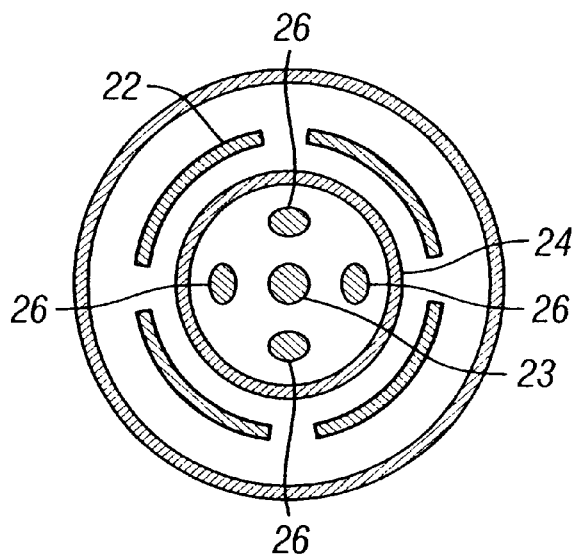
FIG. 6 is a greatly enlarged sectional view of a portion of the diskectomy instrument taken along line 6—6, FIG. 1.

The blades 26 are preferably formed of a hard, biocompatible metal such as stainless steel, titanium, nickel, metal alloy, or the like. But, the blades 26 can be formed of other materials. It should be noted that the blades 26 are rigid. Each blade 26 preferably has an asymmetrical shape as best shown in FIGS. 4–5; however, the blades 26 may be other shapes without departing from the broad scope of the present invention. Preferably, the blades are generally convexly-shaped proximate the at least one sharp edge 32 thereby allowing the blades 26 to naturally find the most concave portions 100a or 100b of a particular vertebra 100.

The blades 26 may be reusable after suitable sterilization as is known in the art, but preferably, the blades 26 are disposable. Accordingly, the blades 26 are preferably removably and movably mounted in the probe 20 within the elongate body 18 of the diskectomy tool 12. In one embodiment, the distal end 12a of the diskectomy instrument 12 is at least partially open or the end of the probe 20 is removable to allow the blades 26 to be removed from the distal end 12a of the diskectomy tool 12. Preferably, however, the blades 26 are removed proximally through the elongate body 18 allowing the end of the probe 20 to be generally closed and bluntly rounded.

Referring to FIGS. 4–5 and 7, each blade has an inner face 30 and an outer surface 32 having at least one sharpened edge 38 extending at least partially between the distal end 26a and the proximal end 26b of the blade 26. The stem mating portion 29 of the blades 26 are configured to cooperatively engage the blade mating portion 23b, 23c of the drive stem 21. Preferably, each blade 26 includes a notch 34 having a retracting ledge 35 defining the stem mating portion 29, and each blade 26 also includes an extending ramp 36. Preferably, each blade 26 has two or more ramps 36 to firmly guide the blade 26 radially outward. The retracting ledge 35 accommodates a portion of the proximal end 23b of the stem end-cap 23 which defines the blade mating portion 23b, 23c of the drive stem 21. The extending ramp 36 cooperates with the dome-shaped surface 23c of the end-cap 23. The end-cap 23 is attached to or integrally formed with the drive stem 21 at the most distal end 21a of the drive stem 21. The end-cap 23 is preferably hemispherically-shaped wherein the proximal end 23b is generally flat and the distal end 23a includes the spherical portion defining the dome-shaped surface 23c. While the stem end-cap 23 of the preferred embodiment is hemispherically shaped, the stem end-cap 23 may have other shapes such as an egg shape, a bullet shape, a conical shape, a pyramidal shape or the like without departing from the broad inventive concept herein. Furthermore, the stem end-cap 23 may also have other cooperative shapes and/or structures as well including for example protuberances and detents. For example, if the blade mating portion 23b, 23c of the drive stem 21 is a protuberance then the stem mating portion 29 of the blade 26 is a cooperatively shaped indentation or the like. Likewise, if the blade mating portion 23b, 23c of the drive stem 21 is an indentation then the stem mating portion 29 of the blade 26 is a cooperatively shaped protuberance. Of course, the blade mating portion 23b, 23c of the drive stem 21 and the stem mating portion 29 of the blade 26 may be other cooperative shapes suitable for engaging one another without departing from the present invention.

Preferably, each blade 26 includes a bidirectional sharp cutting edge 38 spanning both sides of the blade 26. The blades 26 may also include a plurality of sharp cutting edges 38 emanating from the same side of the at least one sharpened edge 38. Alternatively, the blades 26 include only one sharpened edge 28 facing one direction. Thus, during use when the blades 26 are rotated in the cutting direction, the sharpened edges 38 tend to cut but when the blades 26 are rotated in the opposite direction the blades 26 tend not to cut. Of course the blades 26 could be designed to cut in either direction or both directions without departing from the present invention.

The distal end 26a of the blade 26 is preferably blunted or dull to cooperatively engage the biasing cone 25 when the stem 21 pushes the blades 26 with force in the distal direction thereby causing the blades 26 to move distally and radially outward. In an alternate embodiment, the elongate body 18 further comprises a fixed abutment (not shown) configured to engage the ramp 36 when the drive stem 21 is moved distally thereby assisting in extending the blades 26 radially outward.

The probe assembly 20 is mechanically coupled by known methods to either the elongate body 18 or the interior portion of the blade rotation knob 16 such that rotation of the blade rotation knob 16 in turn rotates the probe assembly 20 thereby rotating the blades 26. The blade rotation knob 16 is preferably coupled to the blades 26 and rotating the blade rotation knob 26 causes the blades 26 to rotate in a cutting direction.

The proximal end 26b of the blades 26 is sloped such that the proximal end of surface 32 cooperatively engages an inner wedged surface 24a of the inner sheath 24. Proximal movement of the blades 26 causes a sloped portion of each outer surface 32 to engage the inner wedged surface 24a of the inner sheath 24, thereby causing the blades 26 to also retract inwardly as well as proximally. Optionally, the proximal end 27a of the blade openings 27 also engages the sloped portion of the outer surface 32, thereby assisting the inner wedged surface 24a of the inner sheath 24 in imparting inward movement on the blades 26. Such a configuration provides the surgeon or other user with a mechanical advantage when retracting the blades 26 so that foreign matter can be easily jettisoned from the blades 26 as they are retracted through the blade openings 27.

Figure 9:
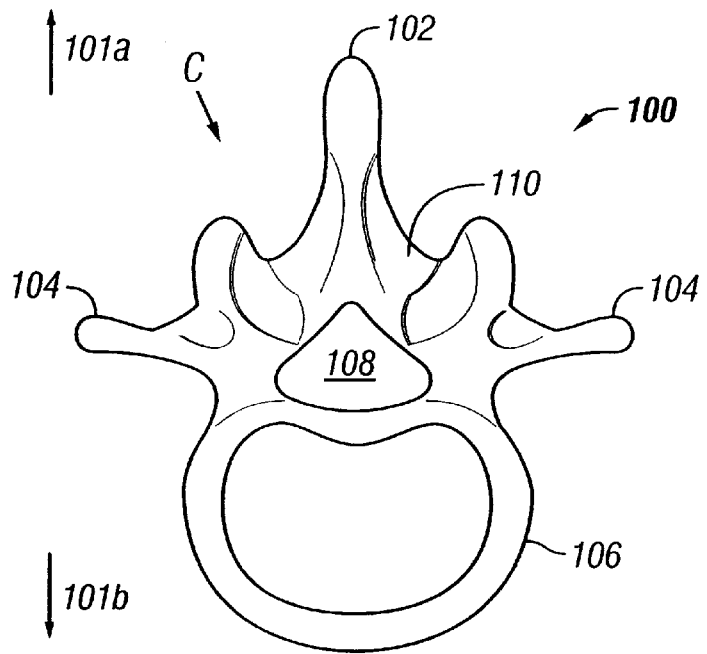
FIG. 9 is a top sectional view of a human vertebrae as is known in the art.
Figure 10:
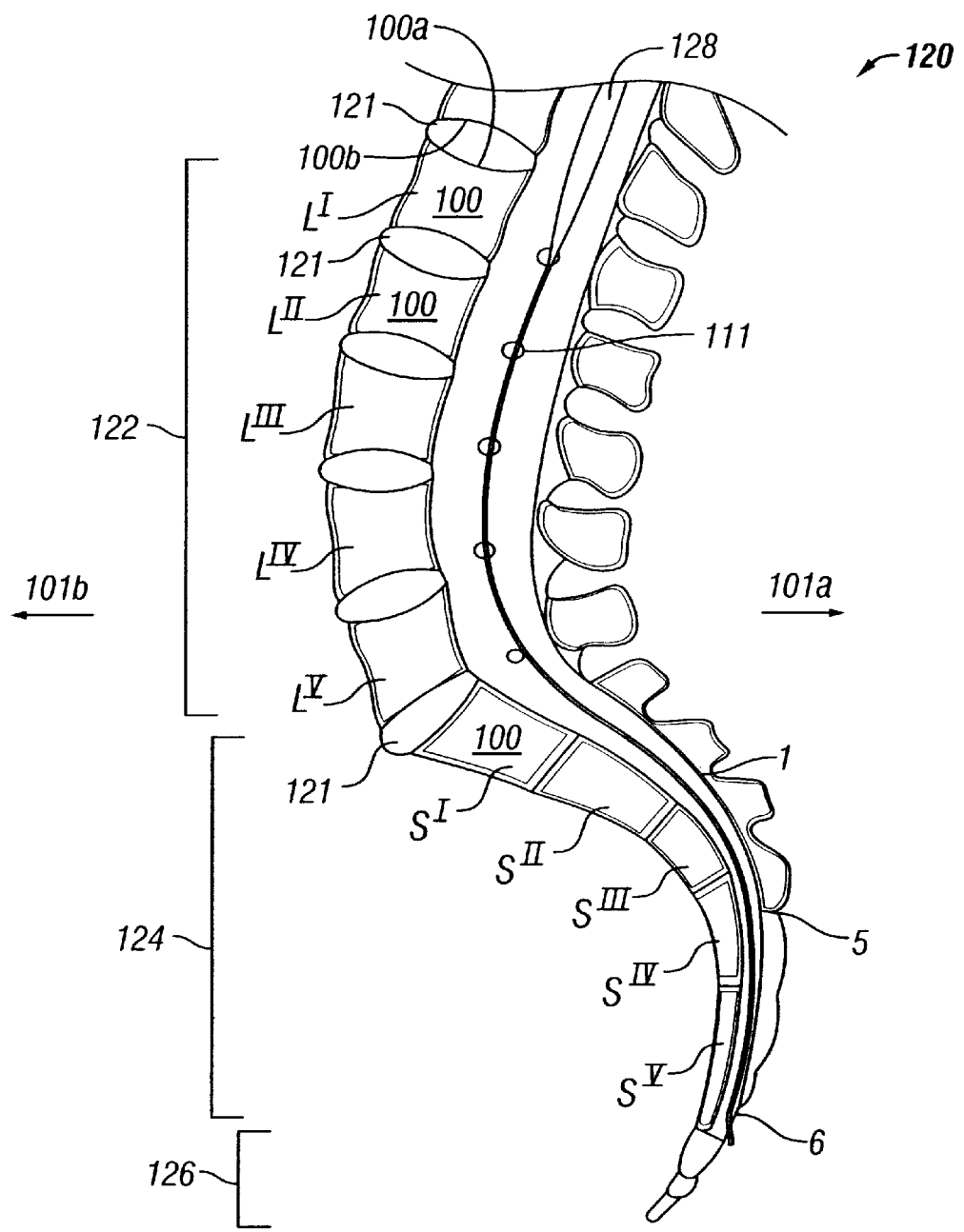
FIG. 10 is a side sectional view of the lumbar and sacral regions of a human spine as in known in the art.

In operation, the blade positioning knob 14 is moved proximally which pulls drive stem 21 in the direction of arrow A (FIG. 2) causing the proximal end 23b of the stem cap 23 to engage the retracting ledge 35, thereby biasing the blades 26 inwardly and proximally toward the inner sheath 24. The distal end 12a of the diskectomy instrument 12 is then inserted through the working tube 50 as is known in the art and into a small gap between a first vertebra and a second adjacent vertebra. Since the distal end 12a of the diskectomy instrument 12 is somewhat blunted, there is minimal risk of damaging ligaments, muscles, nerves, or the like during the insertion process. Preferably, the diskectomy instrument 12 is inserted from the posterior direction 101a at a location off-center such as in the direction of Arrow C (FIG. 9). While the diskectomy instrument 12 is described in the context of microdiskectomy surgery, uses of the instrument 12 are not limited to such surgeries. It is also possible to use the diskectomy instrument 12 in conventional open surgeries such as laminectomies, diskectomies, spinal fusions, and the like.

Figure 3:
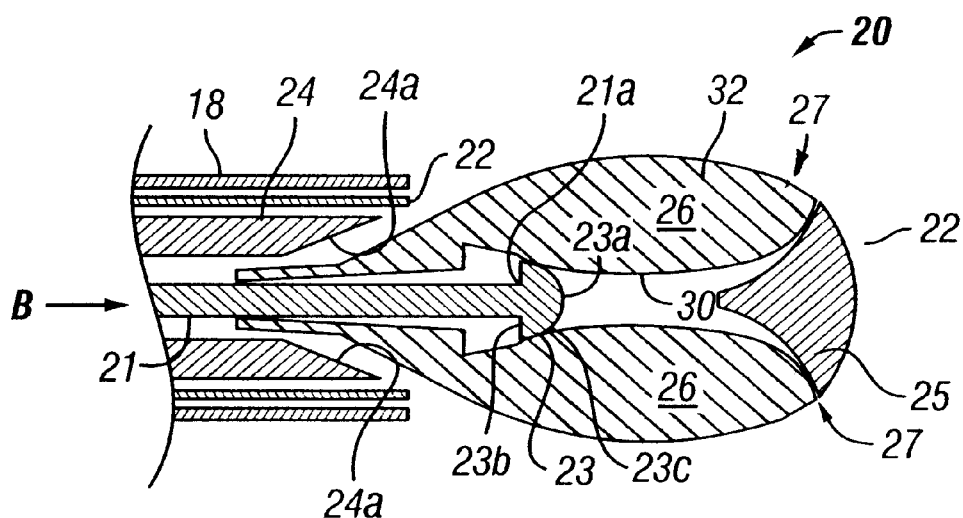
FIG. 3 is a greatly enlarged side sectional view of a portion of diskectomy instrument of FIG. 1 in an extended position.

Once the distal end 12a of the diskectomy instrument 12 is within the intervertebral disk space 121 (FIG. 9), the surgeon can press or rotate the blade positioning knob 14 driving the drive stem 21 distally. The drive stem 21 moves distally in the direction of arrow B (FIG. 3) causing the dome-shaped surface 23c of the stem cap 23 to cooperatively engage the extending ramps 36 of the blades 26 and forcing the distal end 26a of the blades 26 to engage the biasing cone 25 thereby causing the blades 26 to move outwardly such that the sharpened edge 38 extends through the blade openings 27 and beyond the outside of the probe assembly 20.

After the blades 26 have been extended, the surgeon rotates the blade rotation knob 16 in either a clockwise or counter-clockwise direction, depending on the direction of the sharpened edge 38 of the blades 26, causing the probe assembly 20 and the associated blades 26 to rotate therewith and providing a rapid debridement of the nucleus pulposus of the intervertebral disk. Unlike conventional prior art curettes and reamers, the curved and outwardly-biased blades 26 (as best shown in FIG. 5) accommodate the natural concavity of the adjacent vertebrae 100 which significantly reduces the amount of time required to enucleate the disk space 121. If desired, the blades 26 will allow abrasion of the top concave portion 100a of a vertebra and the opposing lower concave portion 100b of the adjacent vertebra to encourage bone ingrowth into devices such as artificial disks, bone grafts, non-bone fusion devices, and the like. If desired, the blades 26 can be used for the partial removal of the end plate (not shown clearly). Due to the size and smooth contour shape of the blades 26, the outer layers of annular ligament and the majority of circumferential edges of the vertebral bodies 106 are able to be preserved which is beneficial to the support of the vertebrae 100 when an interbody device such as an artificial disk or a fusion apparatus is installed after the diskectomy procedure is completed. Such a diskectomy instrument 12 is ideally suited for only removing the nucleus between two adjacent vertebrae 100 while only minimally removing parts of the surrounding bone and annulus.

When the surgeon has completely enucleated or partially enucleated the disk space 121 to the extent desired, the blade positioning knob 14 is moved proximally or rotated in a direction which causes the drive stem 21 to move proximally (i.e., in the direction of arrow A in FIG. 2) again causing the proximal end 23b of the stem cap 23 to engage the retracting ledge 35 of the blades 26 thereby returning the blades 26 to the retracted position. The shape of the blade openings 27, the blades 26, the inner sheath 24, and the probe body 22 naturally deters foreign matter such as fragments of the nucleus pulposus, bone matter and the like from being trapped between the blades 26 and other parts of the diskectomy instrument 12. The diskectomy instrument 12 can then be moved proximally by pulling on the blade rotation knob 16 removing the distal end 12a of the diskectomy instrument 12 from the small gap and subsequently the entire diskectomy instrument 12 from the working tube 50 and/or from the body so that the enucleated disk matter can be removed under fluoroscopy or endoscopy by conventional devices such as forceps, graspers, suction devices, and the like.

While in the presently preferred embodiment there is shown a simple knob (the blade positioning knob 14) connected to the drive stem 21 which is used to radially extend and retract the blades 26, other actuation devices may be utilized without departing from the present invention. The actuator mechanism 13 or simply the actuator 13 is coupled to the proximal end 21b of the drive stem 21 to effectuate proximal and distal movement of the drive stem 21 linearly within the elongate body 18. In one alternate embodiment, the actuator 13 is the positioning knob 14 that is configured to rotate in a first direction to cause the drive stem 21 to move distally and to rotate in a second direction to cause the drive stem to move proximally. In an another alternate embodiment, the blade positioning knob 14 is separately coupled to the actuator 13. Preferably, the blade positioning knob 14 includes incremental indication marks 15 which at least generally correspond to the radial position of the blades 26 relative to the elongate body 18. The incremental indication marks 15 would also provide the surgeon with a gauging or measuring feature of the diskectomy tool 12 allowing the surgeon to measure the intervertebral space 121 prior to inserting any device. The surgeon simply rotates the positioning knob 14 until the blades 26 are firmly touching vertebrae 100 and then can read the distance using the incremental indication marks 15.

FIG. 11 shows another embodiment of an actuator 13'. The proximal end 21b of the drive stem 21 is externally toothed (teeth 21d) and the actuator 13' includes a drive gear 40. The actuator 13' is rotatably mounted to the proximal end 18b of the elongate body 18 in such a manner that the teeth 21d of the drive stem 21 are in mesh engagement with the drive gear 40 of the actuator 13'. Rotation of the drive gear 40 in a first direction causes the drive stem 21 to move distally and rotation of the drive gear 40 in a second direction causes the drive stem 21 to move proximally. One possible rotatable blade positioning knob 14' is depicted as being disposed proximally to a blade rotation knob 16' and has teeth 14a' engaged with the drive gear 40.

FIG. 12 shows another embodiment of an actuator 13" where the proximal end 21b of the drive stem 21 is externally threaded (threads 21e) and the actuator 13" is internally threaded (threads 13a"). The actuator 13" is rotatably mounted to the proximal end 18b of the elongate body 18 in such a manner that the external threads 21e of the drive stem 21 are in threaded engagement with the internal threads 13a" of the actuator 13". Rotation of the actuator 13 in a first direction causes the drive stem 21 to move distally and rotation of the actuator 13 in a second direction causes the drive stem 21 to move proximally by translation of the internal and external threads 13a", 21e", respectively. The actuator 13" preferably includes a plurality of suitable reduction gears 42–43 as is known in the art to enable a user to precisely position the blades 26. One possible rotatable blade positioning knob 14" is depicted as being disposed proximally to a blade rotation knob 16" and has teeth 14a" engaged with the drive gear 41.

In another alternate embodiment (not shown), the drive stem 21 is actuated using scissors-like hand grips which may or may not have mechanical stops or limits for adjusting how far the drive stem is extended distally. It should be recognized that the particular method of actuating the drive stem 21 is not critical to the present invention.

Although the blade rotation knob 16 is depicted as having a knurled or textured surface, the blade rotation knob 16 may also be more complex without departing from the broad scope of the present invention. For example, in another alternate embodiment, the handle may be a two-piece assembly wherein a ratchet mechanism 17 is located between, for example, an inner and outer piece, allowing the surgeon to use partial turns of the blade rotation knob 16 effectuate rotation of the at least one blade in the cutting direction (i.e., to rotate the blades 26 in one direction).

In another alternate embodiment, a more complex mechanical assembly may include a side handle gearedly connected by directional translation gears, such as worm gears, helical gears, bevel gears and the like, to a rotational drive gear (not shown) connected to the probe assembly 20 allowing the surgeon to crank the side handle in a fashion similar to an egg beater thereby rotating the probe assembly 20 including the blades 26 in the cutting direction.

It should be obvious that the relative location of the blade rotation knob 16 and the blade positioning knob 14 is not critical to the present invention. For example, the blade positioning knob 14 may alternatively be disposed on the proximal portion of the elongate body 18 and the blade rotation knob 16 may be disposed proximal to the blade positioning knob 14.

Figure 13A:
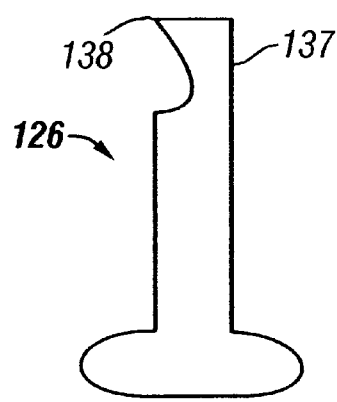
FIGS. 13A–13E are greatly enlarged sectional views of several preferred embodiments of diskectomy blades in accordance with the present invention.
Figure 13B:
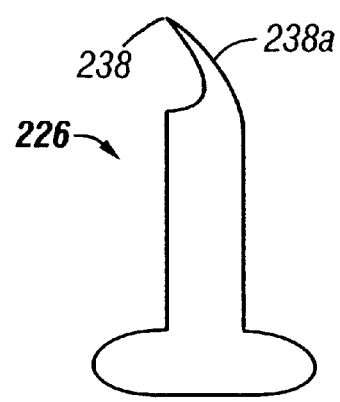
Figure 13C:
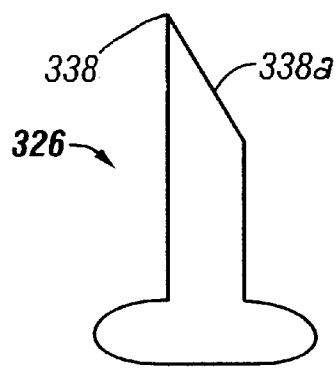
Figure 13D:
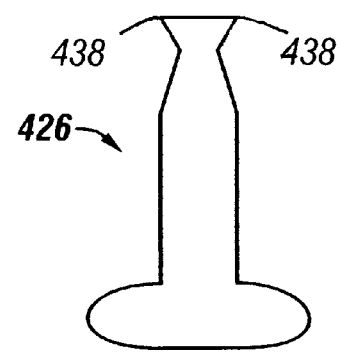
Figure 13E:
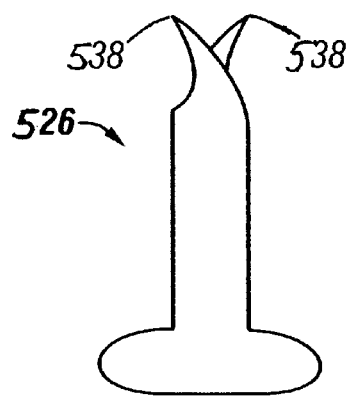

FIGS. 13A–13E are greatly enlarged sectional views of several preferred embodiments of diskectomy blades in accordance with the present invention. FIG. 13A shows a diskectomy blade 126 having a single sharpened edge 138 and a substantially box-like backing 137 for added structural support to the sharpened edge 138 of the diskectomy blade 126. The diskectomy blade 126 is a unidirectional type diskectomy blade which cuts in only one direction. FIG. 13B shows another diskectomy blade 226 having a single sharpened edge 238, however the back 238a of the sharpened edge 238 is generally rounded or sloped. The diskectomy blade 226 is also a unidirectional type diskectomy blade. FIG. 13C shows another diskectomy blade 326 having a single sharpened edge 338 and a generally sloped flat back 338a of the sharpened edge 138, 238, 338. The diskectomy blade 326 is also a unidirectional type diskectomy blade. Obviously, the sharpened edge 138, 238, 338 of all of the unidirectional type diskectomy blades 126, 226, 326 could face in the opposite direction of those shown without departing from the present invention. FIG. 13D shows a diskectomy blade 426 that has a pair of oppositely facing sharpened edges 438. The diskectomy blade 426 is a bidirectional type diskectomy blade which cuts when rotating in either direction (clockwise or counterclockwise rotation). FIG. 13E shows a serrated diskectomy blade 526 having multiple sharpened edges 538 alternately disposed along its length, and therefore, the diskectomy blade 526 is another bidirectional type diskectomy blade.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A diskectomy instrument, comprising:

a) an elongate body having a distal end and a proximal end, the elongate body having at least one blade opening proximate the distal end;

b) at least one blade removably and movably mounted at least partially within the elongate body proximate the at least one blade opening, the at least one blade having a distal end, a proximal end, at least one sharp edge extending at least partially between the distal end and the proximal end, a ramped portion and a stem mating portion; and c) a drive stem movably mounted within the elongate body having a distal end, a proximal end and a blade mating portion, the drive stem being configured to slidably engage the at least one blade when the drive stem is moved distally thereby extending the at least one blade radially outward though the at least one blade opening and the blade mating portion being configured to cooperatively engage the stem mating portion of the blade when the drive stem is moved proximally thereby retracting the at least one blade.

2. The diskectomy instrument of claim 1, further comprising an actuator coupled to the proximal end of the drive stem to effectuate proximal and distal movement of the drive stem linearly within the elongate body.

3. The diskectomy instrument of claim 2, wherein the actuator is a positioning knob configured so that rotating the positioning knob in a first direction causes the drive stem to move distally and rotating the positioning knob in a second direction causes the drive stem to move proximally.

4. The diskectomy instrument of claim 3, wherein the positioning knob includes incremental indication marks which generally correspond to the radial position of the at least one blade relative to the elongate body.

5. The diskectomy instrument of claim 2, further comprising a positioning knob coupled to the actuator wherein rotating the positioning knob in a first direction causes the drive stem to move distally and rotating the positioning knob in a second direction causes the drive stem to move proximally.

6. The diskectomy instrument of claim 5, wherein the positioning knob includes incremental indication marks which generally correspond to the radial position of the at least one blade relative to the elongate body.

7. The diskectomy instrument of claim 2, further comprising a blade rotation knob coupled to the at least one blade wherein rotating the blade rotation knob causes the at least one blade to rotate in a cutting direction.

8. The diskectomy instrument of claim 7, wherein the actuator further comprises a ratchet mechanism coupled between the blade rotation knob and the at least one blade whereby partial turns of the blade rotation knob effectuate rotation of the at least one blade in the cutting direction.

9. The diskectomy instrument of claim 2, wherein the proximal end of the drive stem is externally threaded and the actuator is internally threaded, the actuator being rotatably mounted to the proximal end of the elongate body in such a manner that the external threads of the drive stem are in threaded engagement with the internal threads of the actuator and wherein rotation of the actuator in a first direction causes the drive stem to move distally and rotation of the actuator in a second direction causes the drive stem to move proximally by translation of the internal and external threads.

10. The diskectomy instrument of claim 2, wherein the proximal end of the drive stem is externally toothed and the actuator includes a drive gear, the actuator being rotatably mounted to the proximal end of the elongate body in such a manner that the teeth of the drive stem are in mesh engagement with the drive gear of the actuator and wherein rotation of the drive gear in a first direction causes the drive stem to move distally and rotation of the drive gear in a second direction causes the drive stem to move proximally.

11. The diskectomy instrument of claim 1, wherein the portions of the diskectomy instrument intended to contact internal human body matter are formed of a biologically compatible material selected from the group consisting of stainless steel, titanium, nickel plated metal, a biocompatible metal, a biocompatible alloy, a biocompatible ceramic and a biocompatible polymeric material.

12. The diskectomy instrument of claim 1, wherein the stem mating portion of the blade is an indentation.

13. The diskectomy instrument of claim 1, wherein the stem mating portion of the blade is a protuberance.

14. The diskectomy instrument of claim 1, wherein the at least one blade is disposable.

15. The diskectomy instrument of claim 1, wherein the at least one blade is removed from the distal end of the elongate body.

16. The diskectomy instrument of claim 1, wherein the distal end of the elongate body is substantially closed and generally bluntly rounded.

17. The diskectomy instrument of claim 1, wherein the width of the at least one blade opening is in close tolerance to the width of the at least one blade thereby permitting the at least one blade opening to provide lateral support to the at least one blade during use.

18. The diskectomy instrument of claim 1, wherein the at least one blade is generally convexly-shaped proximate the at least one sharp edge thereby allowing the at least one blade to naturally find the most concave portions of a vertebra.

19. The diskectomy instrument of claim 1, wherein the elongate body further comprises a fixed abutment configured to engage the ramp when the drive stem is moved distally thereby assisting in extending the at least one blade radially outward.

20. The diskectomy instrument of claim 1 in combination with a working tube, the working tube having an elongate housing, a distal end, a proximal end and an interior lumen traversing through the elongate housing, the working tube being configured to be inserted through an incision less than about 50 mm in span.

21. The diskectomy instrument of claim 1 in combination with a working tube, the working tube having an elongate housing, a distal end, a proximal end and an interior lumen traversing through the elongate housing, the working tube being configured to be inserted through an incision less than about 25 mm in span.

22. A diskectomy instrument, comprising:
a) an elongate body having a distal end and a proximal end, the elongate body having a plurality of blade openings proximate the distal end;
b) a plurality of blades removably and movably mounted at least partially within the elongate body, each blade disposed proximate to a respective one of the plurality of blade openings, the plurality of blades each having a distal end, a proximal end, at least one sharp edge extending at least partially between the distal end and the proximal end, a ramped portion and a stem mating portion; and
c) a drive stem movably mounted within the elongate body having a distal end, a proximal end and a blade mating portion, the drive stem being configured to slidably engage each of the plurality of blades when the drive stem is moved distally thereby extending the plurality of blades radially outward through the respective plurality of blade openings and the blade mating portion being configured to cooperatively engage the stem mating portion of each of the plurality of blades when the drive stem is moved proximally thereby retracting the plurality of blades.

23. The diskectomy instrument of claim 22, wherein there are exactly four blades.

24. A diskectomy blade having a distal end and a proximal end for use in a diskectomy instrument, the diskectomy instrument including a body and a drive stem having a blade mating portion, the blade comprising:
a) at least one sharp edge extending at least partially between the distal end and the proximal end,
b) a ramped portion configured to slidably engage with one of the stem of the diskectomy instrument and the body of the diskectomy instrument, and
c) a mating portion configured to couple with the blade mating portion of the diskectomy instrument.

25. The diskectomy blade of claim 24, wherein the blade is reusable.

26. The diskectomy blade of claim 24, wherein the blade is disposable.

27. The diskectomy blade of claim 24, wherein the at least one blade is generally convexly-shaped proximate the at least one sharp edge thereby allowing the at least one blade to naturally find the most concave portions of a vertebra.

28. A method of using a diskectomy instrument, the diskectomy instrument including an elongate body having a blade opening, a blade having a sharp edge, a ramped portion and a stem mating portion, and a drive stem having a blade mating portion, wherein the drive stem is configured to slidably engage the at least one blade when the drive stem is moved distally thereby extending the blade radially outward though the blade opening and the blade mating portion is configured to cooperatively engage the stem mating portion of the blade when the drive stem is moved proximally thereby retracting the blade, the method comprising the steps of:
a) moving the drive stem proximally causing the blade mating portion to engage the stem mating portion of the blade thereby retracting the blade at least partially into the elongate body;
b) inserting a distal end of the diskectomy instrument into a small gap between a first vertebra and a second vertebra of a spine;
c) moving the drive stem distally causing the blade mating portion to engage the blade which in turn moves the blade distally and radially outward;
d) rotating the blade in a cutting direction defined by the orientation of the sharp edge;
e) moving the drive stem proximally causing the blade mating portion to engage the stem mating portion of the blade thereby retracting the blade at least partially into the elongate body; and
f) withdrawing the distal end of the diskectomy instrument from the small gap.

29. The method of claim 28, wherein the diskectomy instrument further includes an actuator coupled to the proximal end of the drive stem to effectuate proximal and distal movement of the drive stem linearly within the elongate body and a positioning knob coupled to the actuator, and wherein step c) includes rotating the positioning knob in a first direction to move the drive stem distally and steps a) and e) include rotating the positioning knob in a second direction to move the drive stem proximally.

30. The method of claim 28, wherein the diskectomy instrument further includes a blade rotation knob coupled to the blade through the elongate housing, and wherein step d) includes rotating the blade rotation knob to rotate the blade in the cutting direction.

31. A method of using a diskectomy instrument and a working tube in outpatient surgery, the diskectomy instrument including an elongate body having a blade opening, a blade having a sharp edge and a partially convex shape, a ramped portion and a stem mating portion, and a drive stem having a blade mating portion, wherein the drive stem is configured to slidably engage the at least one blade when the drive stem is moved distally thereby extending the blade radially outward though the blade opening and the blade mating portion is configured to cooperatively engage the stem mating portion of the blade when the drive stem is moved proximally thereby retracting the blade, the method comprising the steps of:

a) moving the drive stem proximally causing the blade mating portion to engage the stem mating portion of the blade thereby retracting the blade at least partially into the elongate body;
b) inserting a distal end of the working tube proximate a small gap between a first vertebra and a second vertebra of a spine accessible through an incision between about 10mm and about 100 mm in span;
c) inserting a distal end of the diskectomy instrument into the working tube in order to access the intervertebral space between the first and second vertebrae and into the small gap between the first and second vertebrae;
d) moving the drive stem distally causing the drive stem to engage the blade which in turn moves the blade distally and radially outward;
e) rotating the blade in a cutting direction defined by the orientation of the sharp edge so that the convexly-shaped blade finds the most concave portions of the first and second vertebrae;
f) moving the drive stem proximally causing the blade mating portion to engage the stem mating portion of the blade thereby retracting the blade at least partially into the elongate body; and
g) withdrawing the distal end of the diskectomy instrument from the disk space and the working tube.

* * * * *